United States Patent [19]

Mummey et al.

[11] Patent Number: 5,877,331

[45] Date of Patent: Mar. 2, 1999

[54] PREVENTION OF CATALYST ATTRITION AND TAR FORMATION IN MANUFACTURE OF MALEIC ANHYDRIDE

[75] Inventors: Michael J. Mummey, Austin, Tex.; Robert A. Keppel, Chesterfield, Mich.; A. Lamar Reeves, Gonzalez, Fla.

[73] Assignee: Huntsman Petrochemical Corporation, Austin, Tex.

[21] Appl. No.: 968,172

[22] Filed: Nov. 12, 1997

[51] Int. Cl.$^6$ .................................................. C07D 307/60
[52] U.S. Cl. .............................. 549/259; 422/197; 502/21
[58] Field of Search ............................. 549/259; 502/21, 502/34, 38; 422/197

[56] References Cited

U.S. PATENT DOCUMENTS

| | | | |
|---|---|---|---|
| 4,400,306 | 8/1983 | Dria et al. ................................ | 252/431 |
| 4,501,907 | 2/1985 | Kwentus et al. ........................ | 549/259 |
| 4,571,325 | 2/1986 | Nikolov et al. ......................... | 422/191 |
| 4,820,496 | 4/1989 | Sapoff ..................................... | 422/197 |
| 4,994,241 | 2/1991 | Sapoff ..................................... | 422/219 |
| 5,114,685 | 5/1992 | Sapoff ..................................... | 422/219 |
| 5,124,291 | 6/1992 | Bremer et al. ........................... | 502/21 |
| 5,417,938 | 5/1995 | Shelden et al. .......................... | 422/196 |
| 5,484,576 | 1/1996 | Langer et al. ........................... | 422/211 |

OTHER PUBLICATIONS

Mills, reprint of Ceramic Industry, Business News Publishing, "Ceramics and Catalysis," Jun. 1985.

Norton Product Brochure, Norton Chemical Process Products Corporation, "Denstone® Inert Catalyst Bed Supports," ©1993, Serial No. 410027/8/93 DEN–IR.

*Primary Examiner*—Bernard Dentz
*Attorney, Agent, or Firm*—Senniger, Powers, Leavitt & Roedel

[57] ABSTRACT

Improved methods and apparatus for manufacture of maleic anhydride by catalytic oxidation of n-butane or other hydrocarbon having four carbon atoms in a straight chain over a fixed catalyst bed comprising a phosphorus vanadium oxide catalyst. Movement of catalyst bodies with respect to each other and with respect to the walls of the reaction chamber is restrained so as to prevent the catalyst bodies from abrading against each other or the reactor chamber walls in a manner that would cause formation of catalyst fines. Methods and apparatus are also provided for removal of fines from a fixed catalyst bed. The methods of the invention are effective to prevent loss of catalyst from a tubular reactor, and to control degradation of solvent absorbent in a process in which maleic anhydride is separated from the reaction gas by absorption into such a solvent.

24 Claims, 3 Drawing Sheets

FIG.3

PREVENTION OF CATALYST ATTRITION AND TAR FORMATION IN MANUFACTURE OF MALEIC ANHYDRIDE

BACKGROUND OF THE INVENTION

This invention relates to the preparation of maleic anhydride by catalytic oxidation of n-butane or other hydrocarbons having at least four carbon atoms in a straight chain, and more particularly to an improved process in which carryover of catalyst fines in the reaction gases exiting the catalytic reaction chamber is prevented.

Maleic anhydride is produced commercially by catalytic oxidation of n-butane, butenes or other hydrocarbons having at least four carbon atoms in a straight chain. Catalysts for the reaction have active sites comprising phosphorus vanadium oxides. Particularly preferred processes use a tubular reactor containing a fixed bed of phosphorus vanadium oxide catalyst shaped bodies, for example, cylinders, spheres, saddles, trilobes, etc., typically having a principal dimension of at least one eighth of an inch. Most commonly, the fixed catalyst bed is packed into the tubes of a shell and tube heat exchanger, and a salt bath is circulated through the shell of the exchanger for removal of the heat generated by the exothermic oxidation reaction. The reaction gases exiting the reactor contain maleic anhydride product, inert gases, water and other by products including acetic acid, acrylic acid, carbon monoxide and carbon dioxide.

Maleic anhydride is recovered from the reaction product gases by absorption in water or, as described for example in U.S. Pat. 4,118,403, by absorption in an organic solvent such as phthalate ester, preferably an alkyl phthalate. Dialkyl phthalates such as dibutyl phthalate have been used commercially for this purpose. Rich solvent exiting the absorber is stripped under vacuum for recovery of maleic anhydride from the solvent, and lean solvent is recycled to the absorber for further recovery of maleic anhydride from the reaction gases.

Over an extended course of operations, solvents such as dibutyl phthalate are observed to become contaminated with high molecular weight materials, commonly referred to as "tars". As described in U.S. Pat. No. 4,118,403, tars can be eliminated from the system by distilling the solvent, leaving a residue of high tar content which is purged from the system. Provision and operation of solvent distillation facilities adds to the capital and operating cost of a maleic anhydride manufacturing facility. To eliminate this operation, or at least minimize the energy consumed in solvent distillation and the requisite investment in distillation facilities, processes have been developed for extraction of tars from the recycle solvent stream. Such processes are described in U.S. Pat. No. 5,631,387.

While tar extraction offers a signal improvement in a maleic anhydride solvent absorption system, the extraction system involves its own capital and operating costs. Tar formation consumes absorption solvent regardless of how effectively the tars are removed; and the purge of tars through either distillation or extraction inevitably carries out some fraction of unhydrolyzed solvent. Maleic anhydride manufacturing operations would be further optimized, and the costs associated with solvent absorption further minimized, if the rate of tar formation were substantially reduced in the first instance.

Shaped bodies comprising phosphorus vanadium oxide ("VPO") catalysts are relatively soft and frangible. During maleic anhydride manufacturing operations, such catalyst have been observed to deteriorate, causing alterations of flow characteristics in the tubes of the maleic anhydride reactor. Inspection of the reactor during plant turnarounds sometimes reveals a significant loss of catalyst from some or all of the tubes. In exceptional circumstances, tubes can potentially be emptied of catalyst. Loss of catalyst not only reduces productivity of the reactor but also adversely affects yields on n-butane or other starting material. Yield loss may be aggravated by the passage of unreacted hydrocarbon feed gas through tubes which have been emptied of catalyst or suffered substantial catalyst loss.

SUMMARY OF THE INVENTION

Among the several objects of the present invention, therefore, may be noted the provision of an improved process for the manufacture of maleic anhydride by catalytic oxidation of n-butane or other hydrocarbons over a fixed bed of VPO catalyst; the provision of such a process in which maleic anhydride is recovered from reaction product gases by absorption in an organic solvent with reduced formation of high molecular weight by products ("tars"); the provision of such a process in which the capital and operating expense of solvent distillation facilities can be reduced or entirely eliminated; the provision of such a process in which the consumption of absorbing solvent is minimized; the provision of such a process in which loss of catalyst from a fixed bed reaction chamber is substantially reduced; the provision of such a process in which attrition of the shaped catalyst bodies of a fixed catalyst bed is substantially avoided; and the provision of such a process in which high yield and productivity is preserved over a protracted period of operation.

Briefly, therefore, the present invention is directed to an improvement in a process for the manufacture of maleic anhydride by gas phase oxidation of a hydrocarbon having at least four carbon atoms in a straight chain over a fixed catalyst bed comprising discrete catalyst bodies having active sites comprising a phosphorus vanadium oxide catalyst, the fixed catalyst bed being contained within a reaction chamber through which the hydrocarbon, oxygen-containing gas and reaction product gases flow upwardly. In accordance with the improvement the catalyst bodies are restrained to prevent the movement of the bodies with respect to each other, and with respect to any wall of the chamber with which the bed is in proximity or contact, that could otherwise be caused by expansion of the bed or fluidization of any portion of the bed during operation of the reactor. The catalyst bodies are thereby prevented from abrading against one another or a wall of the reactor in a manner that would cause formation of phosphorus vanadium oxide catalyst fines subject to entrainment in the reaction gas stream at the normal operating linear velocities in the reaction chamber.

The invention is further directed to a method for preparing a catalytic reactor for use in the production of maleic anhydride by oxidation of a hydrocarbon having at least four carbon atoms in a straight chain, the reactor comprising a reaction chamber containing a fixed catalyst bed having active sites comprising a phosphorus vanadium oxide catalyst. A purging gas is passed through the reaction chamber for removal from the reaction chamber of phosphorus vanadium oxide catalyst fines contained therein while not removing the fixed bed of catalyst bodies from the chamber. The fines are separated from the purging gas exiting the reaction chamber to substantially prevent emission of phosphorus vanadium oxide catalyst fines into the atmosphere.

The invention is further directed to an improvement in a process for the manufacture of maleic anhydride, the process comprising: preparing a reaction gas by gas phase oxidation of a hydrocarbon having at least four carbon atoms in a straight chain over a fixed catalyst bed comprising discrete catalyst bodies having active sites comprising a phosphorus vanadium oxide catalyst; contacting the reaction gas with a solvent absorbent in an absorption zone for transfer of maleic anhydride from the reaction gas into the solvent absorbent, the solvent absorbent being subject to degradation in the presence of the phosphorus vanadium oxide catalyst; stripping maleic anhydride from the solvent absorbent; and recycling the solvent absorbent to the absorption zone for further absorption of maleic anhydride from the reaction gas. In accordance with the improvement, transport of catalyst fines from the fixed bed to the absorption zone is controlled to inhibit accumulation of catalysts fines in the solvent absorbent, thereby inhibiting degradation of the solvent absorbent.

The invention is further directed to apparatus for use in the manufacture of maleic anhydride by catalytic oxidation of a hydrocarbon in a fixed catalyst bed. The apparatus comprises a tubular reactor comprising a plurality of vertically-oriented tubes, each tube containing a component fixed bed comprising discrete bodies of phosphorus vanadium oxide catalyst, the component beds together comprising the fixed catalyst bed. Restraining means are positioned at the upper ends of the tubes to prevent fluidization of the component beds contained therein and thereby prevent attrition of the catalyst bodies by abrasion against one another and/or against the interior walls of the tube. An absorber is in fluid flow communication with the upper ends of the tubes, the absorber comprising an inlet for reaction gas exiting the tubes, an inlet for solvent absorbent, means for promoting mass transfer between the reaction gas and the solvent absorbent to produce a rich absorbent solution containing maleic anhydride transferred from the reaction gas to the solvent absorbent, an exit for the rich absorbent solution, and an exit for lean gas from which maleic anhydride has been absorbed.

The invention is further directed to an apparatus for removal of catalyst fines from a fixed catalyst bed comprising discrete bodies of phosphorus vanadium oxide catalyst. The apparatus comprises a reaction chamber containing the fixed bed, the reaction chamber comprising a gas inlet and a gas outlet. A source of purging gas is in fluid flow communication with an inlet of the reaction chamber, the source of purging gas being capable of supplying gas at a velocity effective to entrain catalyst fines having a particle size less than about 100 microns and remove the fines from the catalyst bed. A filter is in fluid flow communication with an outlet of the reaction chamber, the filter comprising a porous filter medium, the pore size of which is effective to substantially remove entrained catalyst fines from the purging gas.

The invention is further directed to a fixed bed reactor for preparing maleic anhydride by oxidation of a hydrocarbon reactant gas. The reactor comprises a shell and tube heat exchanger comprising vertically-oriented tubes, a lower head in fluid flow communication with the lower ends of the tubes and having an inlet for hydrocarbon reactant gas and a gas containing oxygen, and an upper head in fluid flow communication with the upper ends of the tubes and having an outlet for discharge of reaction gas from the reactor. Within the tubes are component catalyst beds, each component bed comprising discrete bodies of phosphorus vanadium oxide catalyst, the component catalyst beds together constituting the fixed catalyst bed of the reactor. Means for restraining the catalyst bodies in the tubes prevent movement thereof with respect to each other and with respect to the walls of the tubes.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

In accordance with the present invention, it has been discovered that the formation of tars in a maleic anhydride solvent absorption system can be minimized by controlling carryover of VPO catalyst fines from a fixed bed reactor to the maleic absorber. Catalyst fines have been shown to promote hydrolytic degradation of alkyl phthalate type solvents, leading to the formation of tars in the solvent circuit. Catalyst fines are generated by physical degradation of the shaped catalyst bodies in the fixed bed of the reactor. As noted, these shaped bodies are soft and relatively frangible. It has been discovered that a prominent cause of the formation of fines is abrasion between adjacent catalyst bodies and/or abrasion between the catalyst bodies and a wall of the reaction chamber. Such abrasion results from movement of the catalyst bodies due to fluidization or expansion of at least part of the fixed catalyst bed by the reactant gases flowing therethrough.

Gas hourly space velocities in maleic anhydride reactors are typically in the range of 1600 to 2600 $h^{-1}$ with linear superficial velocities at the exit of the tubes falling in the range of 2.5 to 7.0 m/sec. Since the void fraction in the catalyst column in the tube is typically between about 40% and about 60%, actual velocities in the catalyst bed at the exit of the tube may range from 4 to 18 m/sec., more commonly 7 to 15 m/sec. Such velocities are well above the minimum velocities effective to entrain fines of the particle size obtained by physical degradation that may be caused by abrasion of VPO shaped body catalysts. Such fines typically have a particle size substantially in the range of 2000 to 40$\mu$. In a process wherein maleic anhydride is removed from the reaction gas stream by solvent absorption, fines that are entrained in the reaction gases are carried over into the absorber where a significant portion of the fines are captured by the liquid solvent stream.

The size of commercial VPO shaped catalyst varies. Generally, however, all commercial catalysts adapted for use in fixed bed operations have a principal dimension of at least ⅛" and a body volume of at least about 0.02 cc. Generally, the reaction gas flow velocities in a tubular maleic anhydride reactor are not sufficient to substantially fluidize the component bed of catalyst bodies (i.e., the column of catalyst bodies) contained in a tube of commercial tubular reactor. However, in high productivity operations, the normal gas velocities may be high enough to cause incipient fluidization or expansion of at least a portion of the bed, and temperature excursions or pressure surges may further contribute to partial fluidization. Moreover, variations among the tubes with regard to the amount of catalyst bodies comprising the component of the fixed bed contained in a tube, variations among the tubes in configuration of the flow path through the void space within the tubes, and vagaries in distribution of gas flow across the tube face and entry losses into the tubes may cause initial variation in the flow rate among the tubes, potentially resulting in velocities close to incipient fluidization in some tubes even where the average flow rate is well below the fluidization rate.

Commonly, tubular reactors for the production of maleic anhydride are oriented vertically, with gas flowing upwardly through the tubes. Fluidization may be minimized where the gas is caused to flow downwardly through the tubes, since fluidizing forces are resisted by the catalyst support at the bottom of the tubes. However, upward flow of reaction gases is preferred for a maleic anhydride reactor, and the vast majority of commercial reactors operate in an upflow mode. The preference for upflow derives from the principle that effective heat transfer is promoted by causing reaction gases and cooling medium to flow co-currently through the reactor, so that the highest temperature of the cooling medium, and the lowest driving force for heat transfer, are encountered in the region of the reactor where the driving force for the reaction and the rate of heat generation are lowest. Since practical considerations ordinarily dictate that the salt bath used to cool the reactor tubes flow upwardly through the shell, the reaction gases are preferably caused to flow upwardly inside the tubes.

In an upflow reactor the gas pressure is lowest and gas velocity highest at the top of the tube. Because of these factors, and further because the weight load of the column of catalyst bodies in the tube is lowest in this zone, the tendency to fluidization is the greatest in that portion of the component bed nearest the top of the tube. Thus, fluidization is most likely to occur in that zone. Even though the velocity may not be sufficient to cause entrainment of the catalyst bodies, incipient fluidization or expansion may nonetheless occur in an upper zone of the bed. Expansion or fluidization involves movement of the catalyst bodies relative to each other and relative to the wall of the tube. The resulting abrasion of the catalyst bodies often results in the formation of fines, entrainment of fines in the gas stream and removal of fines from the tube.

Once abrasion, formation of fines and entrainment of fines have commenced, the process of catalyst attrition may become progressive and self accelerating. As the fines are removed from a reactor tube, the void space in the upper zone increases, the flow resistance within the tube correspondingly decreases, and for a given pressure differential across the reactor the gas flow rate through the tube increases. Both the increased velocity and the loss of catalyst from the upper portion of the component bed of catalyst bodies tend to cause the zone of incipient fluidization or expansion to extend further down into the component bed. This in turn causes further physical degradation of catalyst bodies, formation of additional fines, entrainment of fines and loss of catalyst. Self sustaining and self accelerating loss of catalyst can be especially severe in any tubes where the process becomes preferentially established.

Fines entrained in the reaction gases exiting the maleic anhydride reactor are carried over into the absorber. The absorber typically comprises means for enhancing gas/liquid contact, which comparably enhances the occasion for contact of the entrained fines with the solvent absorbent and capture of fines by the solvent stream. As the maleic is removed by stripping from the solvent, the fines remain in the liquid phase. Because of their small particle size, they tend to remain suspended in the liquid and to accumulate in the recirculated solvent. There they remain available for promotion of reactions by which the solvent is degraded.

In the case of phthalate esters, it has been found that the presence of VPO catalyst fines promotes hydrolytic cleavage of the ester linkage. Because of their small particle size and high surface to volume ratio, even a low concentration of fines in the solvent may have a deleterious effect. VPO promoted hydrolysis of a dialkyl phthalate typically yields the monoester and free phthalic acid. By a further reaction sequence that is not fully understood but is also believed to be promoted by the presence of VPO catalyst fines, the products of hydrolysis are converted to high molecular weight substances constituting "tars." . Since they are of lower volatility than the solvent, the tars are not removed in stripping of maleic anhydride from the solvent, and instead accumulate in the recirculating solvent stream. It is considered undesirable to allow the tar level in the recirculating solvent to rise above about 3% by weight.

Tars can be eliminated from the circulating solvent either by distilling the solvent in accordance with the process of U.S. Pat. No. 4,118,403 and/or by extraction of the tars per the processes of U.S. Pat. No. 5,631,387. However, the greater the rate of tar generation, the greater the consumption of solvent, and the greater the investment in a distillation and/or extraction system and the higher the operating cost thereof.

In accordance with a process of the invention, means are provided in the maleic anhydride reactor for restraining the catalyst bodies to prevent movement thereof with respect to each other and with respect to the wall of the tube. Preventing such movement of the catalyst bodies prevents physical degradation thereof that may otherwise result from the catalyst bodies abrading each other and being abraded by moving contact with the reactor tube wall. Thus, the formation of fines is substantially minimized, as is any carryover of fines into the absorber of a maleic anhydride solvent absorption system. This in turn minimizes hydrolytic degradation of the solvent and formation of tars.

Over the course of protracted operations, inhibiting catalyst movement and catalyst attrition is also effective to prevent any significant loss of catalyst from the reactor tubes, and thereby prevent any significant increase in variation among the tubes of the reactor with respect to the flow resistance presented by the component catalyst beds in the tubes to passage of gas through the tubes. This in turn prevents any significant increase in variation of the gas flow rate among the tubes.

Figure 1:
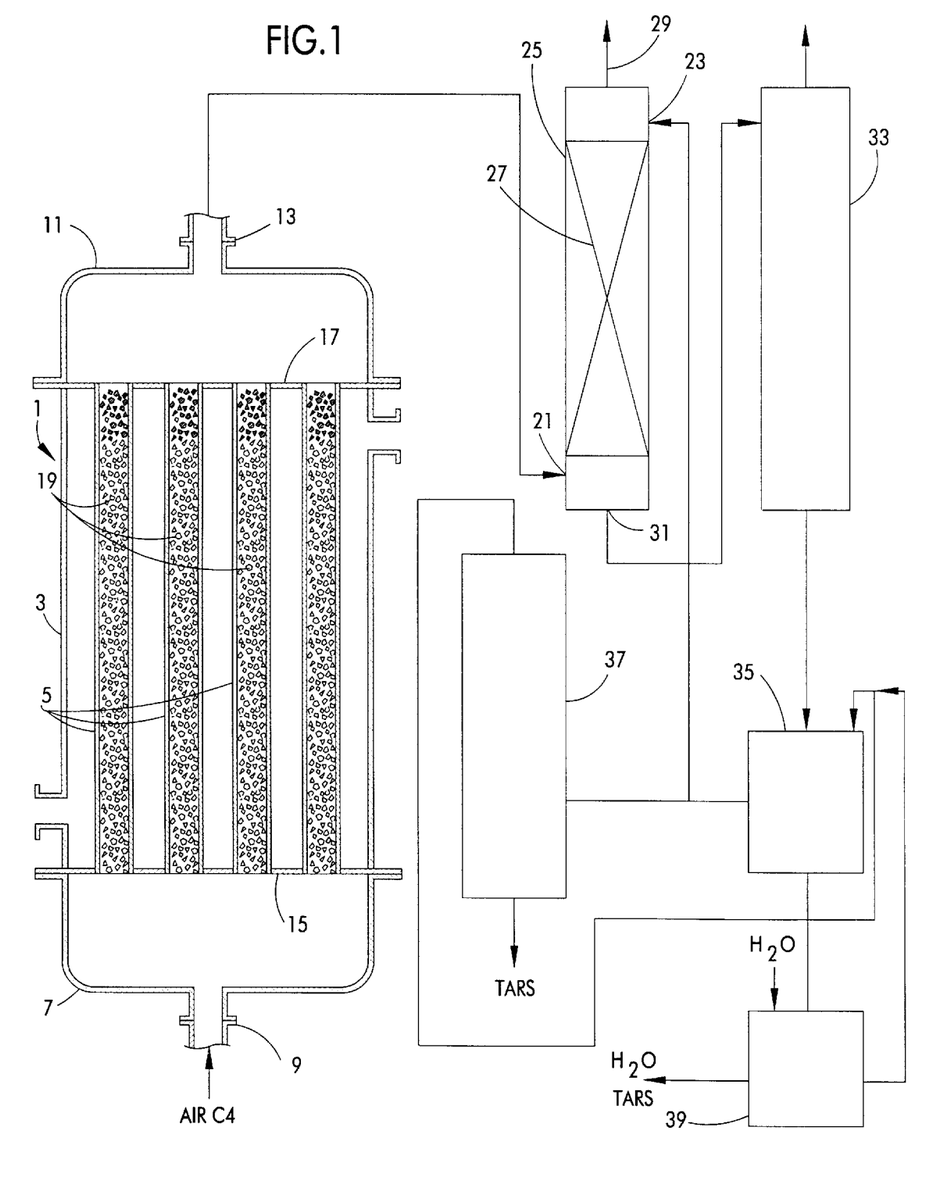
FIG. 1 is a schematic flow sheet of a process for the manufacture of maleic anhydride in which the process and method of the invention may be implemented.

FIG. 1 illustrates a flow sheet and apparatus in which the process of the invention may be carried out. Shown at 1 is a tubular reactor comprising a shell and tube heat exchanger, having a shell 3, vertically oriented tubes 5, a lower head 7 having a gas inlet port 9, and an upper head 11 having a gas exit port 13. Tubes 5 of the reactor are fixed in lower and upper tube sheets 15, 17 and are packed with shaped catalyst bodies to provide in each tube a component bed 19 of VPO catalyst bodies. Taken together, the columns of catalyst comprising component beds 19 constitute the fixed catalyst bed of the reactor, the combined tubes 5 constituting the reaction chamber. Inlet port 9 is in fluid flow communication with a source of a feed gas comprising n-butane and air, which is introduced into the reactor through the inlet port. n-Butane is oxidized over the VPO catalyst bed to form reaction product gas comprising maleic anhydride product, inert gases, water, and other by-products of the reaction such as acetic acid, acrylic acid, carbon monoxide and carbon dioxide. Via exit port 13, the tops of the tubes are in fluid flow communication with an absorber, e.g., an absorption tower 25 for recovery of maleic anhydride from the reaction gases produced in the reactor. Reaction product gas exiting the reactor through port 13 flows to an inlet port 21 at the lower end of absorption tower 25. A solvent such as dibutyl phthalate is introduced into the top of the absorber through a port 23 and flows downwardly through the tower countercurrently to the upwardly flowing gas stream. The absorber contains means 27 for promoting gas/liquid contact and mass transfer. Maleic anhydride is absorbed into the liquid phase, the gas phase exits the tower through a port 29 at the top of the tower, and a solvent stream rich in maleic anhydride exits the absorber through a bottom port 31. The rich solvent stream is directed to a stripping column 33 where maleic anhydride is removed from the solvent by stripping under vacuum. Lean solvent exiting the stripping column is directed to a lean solvent storage tank 35, and thence returned to the top of the absorber. Tars formed in the circulating solvent are eliminated by distillation of the solvent in a solvent still 37 per the disclosure of U.S. Pat. No. 4,118,403, and/or by extraction with water in an extraction system 39 per the disclosure of U.S. Pat. No. 5,631,387, both of which patents are expressly incorporated herein by reference.

Figure 2:
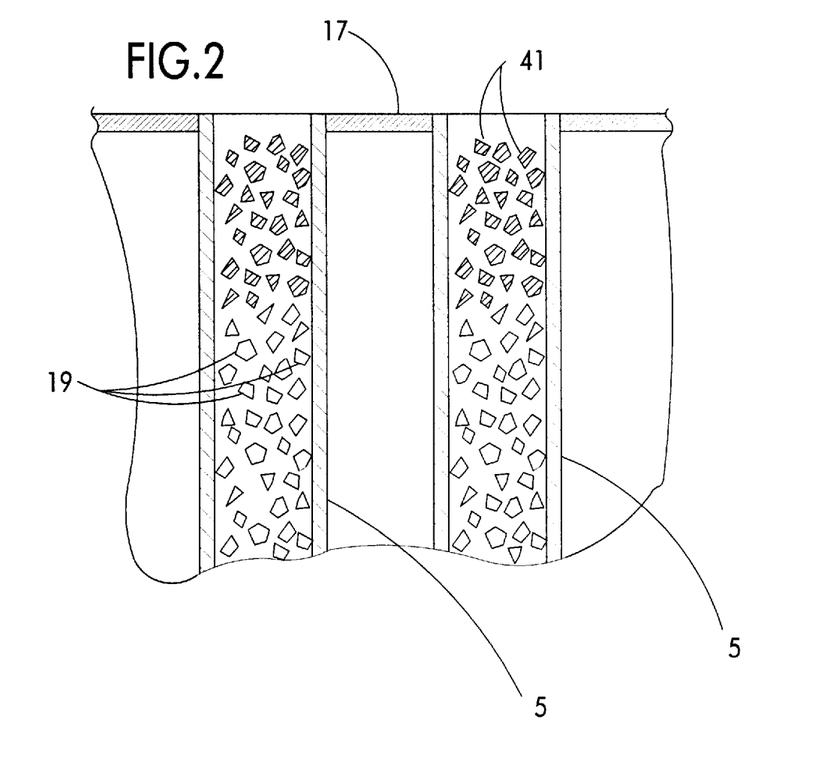
FIG. 2 illustrates a preferred restraining means for preventing fluidization of any portion of a component bed of a fixed catalyst bed in a tubular reactor for the manufacturer of maleic anhydride.

Various restraining means associated with reactor tubes 5 can be used to restrain movement of the catalyst bodies of the fixed bed under the influence of the gas velocities otherwise sufficient to expand or fluidize any portion of the catalyst bed within the tubes. As illustrated in FIG. 2, a preferred restraining means comprises a restraining bed of discrete relatively dense bodies 41 in each tube 5, the restraining bed being positioned above but in contact with and bearing down on the component bed of catalyst bodies 19 within the tube. Preferably, the size and shape of discrete dense bodies of restraining bed 41 is such that the pressure drop per unit length along the gas flow path is not substantially higher in the restraining bed than in the component bed of catalyst bodies within said tube. More particularly, it is preferred that the discrete dense bodies of the restraining bed are of approximately the same average size but substantially higher density than the catalyst bodies within the tube. Preferably, the ratio of the apparent density of the individual dense bodies to the apparent density of the catalyst bodies is at least about 1.0. More preferably, that ratio is at least about 1.5, but bodies of relatively low surface to volume index (see below) can serve effectively as restraining means even if the apparent density of the individual dense bodies is approximately the same as the density of the individual catalyst bodies. The apparent density of the individual dense bodies is preferably at least about 1.5 g/cc, preferably between about 2 and about 9 g/cc. Ceramic bodies useful in a fluidization restraining bed generally have an individual body density of about 2.0 to about 3.0 g/cc, while metal bodies (such as, e.g., stainless steel) preferably have an individual body density in the range of about 4.0 to 9.0 g/cc. Materials of greater density can be used but are generally unnecessary. By comparison, the apparent density (geometric density) of shaped VPO catalyst bodies is typically between about 1.3 and about 2.0 g/cc. For example, VPO trilobe catalysts sold under the trade designation MARS V by Huntsman Corporation have an apparent shaped body density of about 1.7 g/cc.

The average individual body volume of both the catalyst and the dense bodies is at least 0.02 cc, more preferably between about 0.03 and about 0.20 cc. However, the shape and surface to volume ratio preferably differ. Catalyst bodies are preferably of relatively complex shape, e.g., trilobes, of relatively high surface to volume ratio, while the dense bodies of the restraining bed are preferably simple shapes, most preferably spheres, of low surface to volume ratio. For example, the dense bodies should preferably have a surface to volume index no greater than about 10, more preferably not greater than about 8, surface to volume index being defined by the expression $(A/V)d$, where A=external surface area, V=body volume and d=principal dimension. Commercial catalysts on the other hand generally have a surface to volume index greater than about 10, more preferably at least about 12. High surface to volume ratio enhances the effectiveness of the catalyst. Low surface to volume ratio minimizes the drag forces tending to fluidize the dense bodies. The bulk density of the restraining bed is preferably at least about 1.0 g/cc, more preferably between about 1.1 and about 5 g/cc, most preferably between about 1.3 and about 1.7 g/cc for ceramic dense bodies. For metal dense bodies, the bulk density of the restraining bed is preferably in the range of about 2 to about 5 g/cc. By comparison, the bulk density of the fixed catalyst bed is usually in the range of between about 0.5 and about 1.0 g/cc. Trilobe VPO catalysts having a principal dimension of about ¼41 have a bulk density of about 0.65, trilobe VPO catalysts having a principal dimension of about 5/32" have a bulk density of about 0.75, and ¼" cored cylinders have a bulk density somewhat less than 1.0.

Typically, the depth of the restraining bed 41 is at least about 1" (2.5 cm), more preferably between about 5" (12.7 cm) and about 12 " (30 cm). For metal dense bodies the optimal bed depth may be shorter, e.g., 2" to 5". At these depths, the weight of the restraining bed is sufficient to prevent incipient fluidization at the top of the component bed of catalyst bodies within any of the tubes 5 at reaction gas linear flow velocities 1.6 times the normal average reaction gas velocity in the fixed bed. Generally, the weight of said restraining bed is sufficient to prevent incipient fluidization at the top of the component bed at linear gas flow velocities of at least about 2.0 m/sec, more preferably at least about 3.0 m/sec.

While the restraining bed 41 of FIG. 2 is preferred, other restraining means may be employed in vertical tubular reactors through which the gas flow is upward. For example, the restraining means may comprise a spring positioned in a tube 5 and disposed to exert downward force on the component bed of catalyst bodies within the tube. For example, the spring may be fixed at at least one location against movement with respect to a reactor tube but have a free end that is urged against the top of the component bed of catalyst bodies within the tube. The end of the spring in contact with the component bed of catalyst bodies is free to move relative to the tube to impose the requisite downward force despite any shifting or settling of the catalyst bodies within the tube.

A further alternative restraining means suitable for either an upward or downward flow reactor may, for example, comprise a cage within which catalyst bodies are disposed throughout the tube, or any portion thereof such as the upper zone of the component bed of an upward flow reactor in which the susceptibility to fluidization is the greatest. The cage comprises wire or rod members distributed through the portion of the bed through which the cage extends, such members being positioned to restrain movement of catalyst bodies bearing thereagainst.

In a still further alternative for an upward flow reactor, the restraining means comprises a monolithic element permeable to gas flow and free to move relative to tube 5 to impose downward force on the bed catalyst bodies within the tube despite any shifting or settling thereof. Advantageously, such compacting means may be have a honeycomb structure.

Whatever the design or selection of restraining means, the employment thereof is effective over protracted manufacturing operations to substantially minimize: the fluidization or expansion of any portion of the component catalyst bed within the tube; the loss of catalyst from the reactor; emptying of reactor tubes; the concentration and cumulative amount of fines exiting the reactor and trapped in the circulating absorbent; hydrolytic attack on the solvent absorbent; and formation of tars in the solvent circuit. Accordingly, high productivity and yield is consistently realized, consumption of solvent is at a minimum, and solvent distillation and/or extraction may be eliminated, or at least the capital and operating cost thereof kept to a minimum.

The process of the invention is especially advantageous in high productivity operations in which the average linear velocity of the gas approaches the fluidization velocity in some portion of the catalyst bed. High productivity operations in a vertical tubular reactor with upflow of the gas in the tubes may be characterized, for example, by an average superficial gas velocity in the fixed catalyst bed which is at least 90% of the fluidization velocity in the upper zones of component beds. In such operations, the risk of fluidization is typically the greatest in the upper 10% of the height of the component bed in the tube. In accordance with the process of the invention, the reactor may be operated without significant loss of catalyst over a protracted period of, for example, 24 months or more, preferably at least about 36 months, at an average velocity at least 75 to 80%, preferably 90%, more preferably between about 110% and about 120% of the fluidization velocity in such upper zone. At such velocities, the reactor may be operated in single pass mode over the aforesaid protracted periods to maintain a productivity not lower than 3.8 lb/ft$^3$/hr, usually at least about 4.2 lb/ft$^3$/hr, and a yield not lower than about 45 mole % of theoretical, usually not lower than 47–48%.

As noted above, however, abrasion of catalyst bodies during reactor operations is not necessarily the only source of fines that may be carried out in the reaction gases exiting a maleic anhydride reactor. Fresh catalyst loaded into the reactor tubes may contain fines, and fines may be formed in the reactor loading procedures by abrasion of catalyst bodies unavoidably occurring in that procedure. This problem can arise in either upflow or downflow reactors.

Further in accordance with the invention, therefore, a method is provided for removal of fines from the fixed catalyst bed to prepare the reactor for production of maleic anhydride. After packing of the reactor has been completed, a purging gas is passed through the reaction chamber for removal of the fines contained in the catalyst charge within the tubes. This process and apparatus useful therein are illustrated schematically in FIG. 3. Removal of the fines may be accomplished, for example, by connecting a compressed air source 43 to inlet port 9 on bottom head 7 of the reactor, and blowing compressed air through tubes 5. For removal of fines, air is blown through the tubes at a velocity of at least about 0.5 times, preferably between about 0.8 and about 1.2 times the normal velocity of reaction gases during operation of the reactor for the production of maleic anhydride. Fluidization or expansion of the bed during this operation is preferably prevented by installation of restraining means as described above. The restraining means are preferably adapted to exert sufficient restraining force to prevent incipient fluidization at the velocities employed for initial fine removal. However, even if incipient fluidization happens to develop at the top of the bed (or beyond) during initial purging of the bed, the amount of fines produced in this manner is nominal, and such fines are removed by the purge. Most preferably, the air velocity is at least about 2.7 m/sec., more preferably between about 2.9 and about 3.5 m/sec.

Blowing a purging gas through the reaction chamber as described above is effective to entrain and substantially remove from the bed catalyst fines having a particle size less than about 100$\mu$, and under preferred conditions all or substantially all fines having an average particle size less than about 1000 microns. To achieve the most effective removal of fines from the reactor, the purging gas is not passed through the tubes at a constant rate, but instead is passed intermittently. Passing the gas through the tubes in several discrete increments makes it possible to remove not only the fines which find a clear flow path through the component bed within a tube, but also to remove those particle which become entrapped in crevices or niches within or between catalyst bodies, or between catalyst bodies and the tube wall. Intermittently interrupting, or at least substantially slowing the flow of purging gas allows the trapped particles to fall back down under the influence of gravity and be picked up by the next or a later burst for removal from the bed. Preferably, the purging gas is passed through the reactor in at least about two, more preferably about 3 to 5 discrete increments of at least about ten minutes. In each increment, de-dusting gas superficial velocity is ramped up over a period of five to ten minutes to a maximum rate of at least about 1.4 m/sec, and preferably to a maximum rate of about 2 to 3.5 m/sec, then continued at such maximum flow rate for a period of preferably between about twelve minutes and about ninety minutes. At the end of each flow increment, either the air flow is terminated or the flow rate is reduced by between about 50% and about 100% for a period of typically about one to about five minutes. Then the flow is ramped up for the next purging increment. In some instances, it may even be advantageous to periodically reverse the direction of purging gas flow to help dislodge particles that may otherwise be difficult to move. However, the final burst should very preferably be in the direction of normal gas flow, so that any small particles which remain trapped against removal by the purging gas will also be resistant to later removal by reaction gases during manufacturing operations.

In order to prevent deterioration of the VPO catalyst due to absorption of moisture during the purging operation, the catalyst is preferably preheated to a temperature of at least about 120° C., more preferably between about 140° and about 200° C. via passage of heated air through the shell of the reactor, or alternatively by passing heated air through the tubular reaction chamber, preferably in the normal direction of process gas flow through the reactor. In a further alternative, dry air may be used for the purge, e.g., air having a dew point below about 10°, more preferably below about −20 C.

Figure 3:
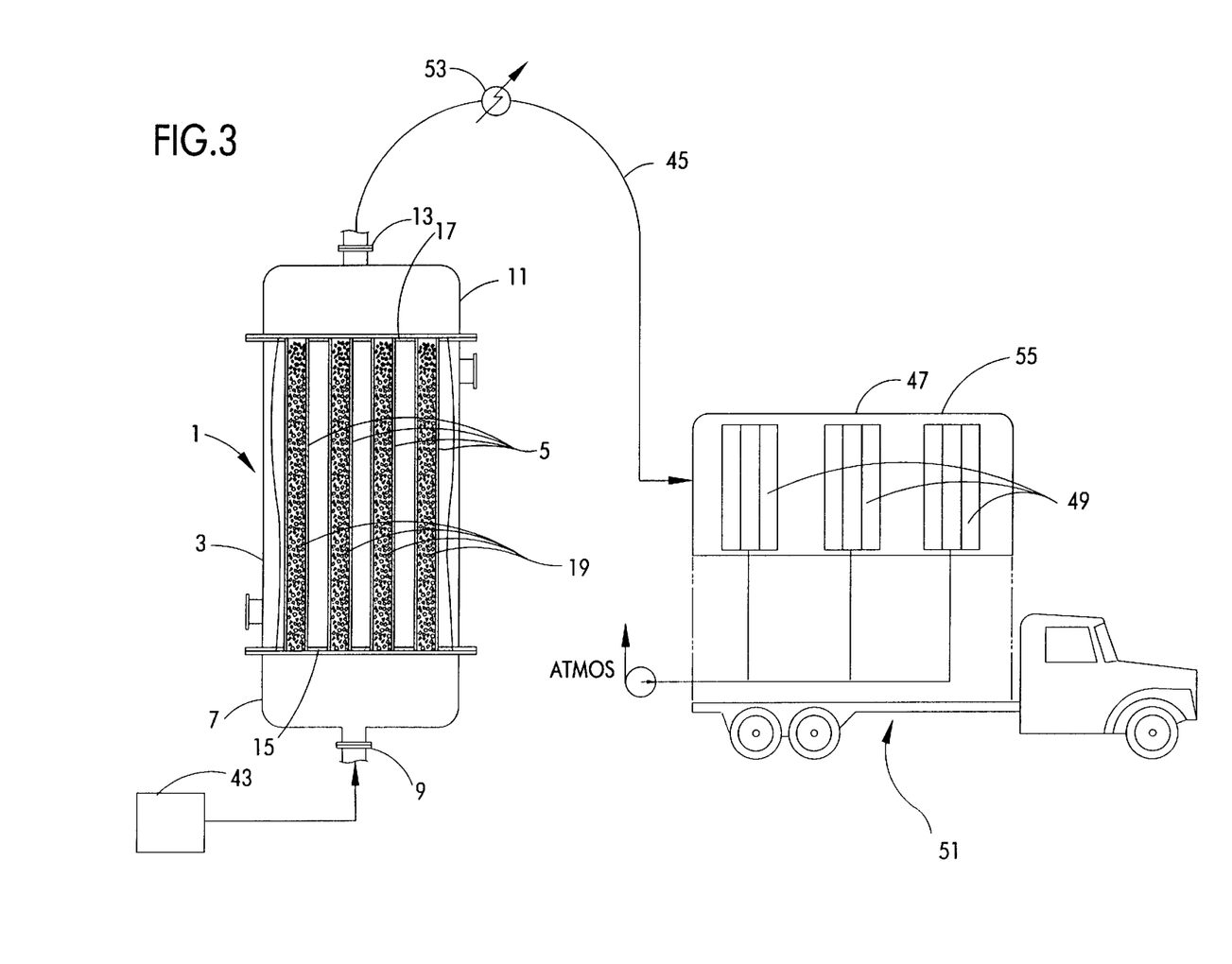
FIG. 3 is a schematic flow sheet of a method for removing catalyst fines and dusts from the fixed catalyst bed of a tubular maleic anhydride reactor prior to the startup thereof.

Air laden with catalyst fines exits the reactor via port 13 on head 11 and is passed through a process gas cooler 53, and is directed through exit line 45 to a filter 47 for removal of the fines from the gas. Filter 47 advantageously comprises a bank of cartridge filters 49 mounted in a housing 55. Preferably, the dust-laden air is cooled in heat exchanger 53 to a temperature of not greater than about 100° C., preferably between about 80° and about 95° C. Air from the filter is discharged to the atmosphere. Collection of the fines in filter 47 prevents potentially unacceptable emissions of VPO catalyst dust into the working area and the environment. Preferably, the filter is constructed of fabric or fibers and has a pore size of between about 5 and about 50μ, more preferably between about 10 and about 30μ. Such a filter is effective for removal of at least about 99% by weight of the fines entrained in the purging gas.

After completion of the de-dusting operation, flow of compressed air is terminated, and lines connecting the catalyst bed to the filter are cleared of residual catalyst fines by operation of a blower 57, which draws air through those lines and through the filter. After the lines have been cleared, the filter is back-pulsed to remove the fines.

Since the filter is not used in ongoing operation, it preferably is not permanently installed but is made portable for transfer to and from the plant site as needed. As illustrated in FIG. 3, filter housing 55 and blower 57 are mounted on a vehicle such as truck or trailer 51. Alternatively, these elements may be skid mounted or otherwise conveniently provided in permanent or portable form.

As indicated above, the de-dusting method of the invention is applicable to both upflow and downflow reactors.

Using the methods of the invention in controlling the transport of catalyst fines into the absorber of a solvent absorption system for recovery of maleic anhydride from catalytic reaction product gas, a substantial reduction is achieved in the formation of tars that otherwise result from degradation of the solvent absorbent. When used, e.g., in conjunction with an extraction system such as that described in U.S. Pat. No. 5,631,387, accumulation of tars can be limited to no greater than about 3% by weight of the circulating absorbent after substantially continual operation over a period of at least about 24 months, even 36 months. Moreover, such the accumulation can be so limited without the necessity of distilling the solvent at any time during such 24 or 36 month period.

The following examples illustrate the invention:

EXAMPLE 1

Samples of each of the following catalysts was ground to pass through a 100 mesh screen: a VPO catalyst sold by Huntsman Corporation under the trade designation E326 (designated hereinafter as "MARS IV X2"), which had been activated in the manner described and claimed in U.S. Pat. No. 5,137,860; a VPO catalyst described and claimed in U.S. Pat. No. 4,632,915 or 4,670,415 and sold by Huntsman under the trade designation E307 (designated hereinafter as "MARS III"); and a modified VPO catalyst sold by Huntsman under the trade designation E326 (designated hereinafter as "MARS IV X"), which had been air calcined and then activated in the presence of nitrogen and steam.

Dibutyl phthalate was introduced in 250 ml aliquots to each of fifteen separate 500 cc round bottom flasks, each containing a magnetic stirrer. VPO catalysts were added to twelve of these flasks. In one of these flasks, MARS IV X was added in a proportion of 0.1% by weight. In the other eleven flasks to which catalyst was added, the catalyst concentration of 2% by weight. Water in a proportion of 1% by weight was added to seven of the flasks containing VPO catalyst and to one of the blank flasks. No water was added to the remaining five flasks containing catalyst or to the remaining two blank flasks. Each of the flasks was heated to an elevated temperature within about 20 minutes and maintained at that temperature for 24 hours. The temperature was maintained constant in each flask but varied among the flasks. After 24 hours, the material in each flask was cooled and filtered through a medium glass frit, 150 ml filter funnel into a 250 ml filter funnel. A sample was then taken and placed in a 30 cc crimp sealable sample vial. The sample of dibutyl phthalate obtained from each of the flasks was observed for color and analyzed for monobutyl phthalate and phthalic acid. The test conditions and appearance of the dibutyl phthalate after 24 hours heating are set forth in Table I. Analyses of the samples and a comparative analysis of the dibutyl phthalate starting material are set forth in Table II. Change in composition of each sample by comparison with the starting dibutyl phthalate material is set forth in Table III.

TABLE I

DBP SOLVENT DECOMPOSITION STUDIES PROTOCOL

| SAMPLE NUMBER | TEMPERATURE (C) | SOAK TIME (HOURS) | WATER CONCENTRATION (PERCENT) | CATALYST TYPE | CATALYST PERCENT | COMMENT |
|---|---|---|---|---|---|---|
| 24 B | N.A. | N.A. | N.A. | N.A. | N.A. | STARTING MATERIAL |
| 20 B | 145 | 24 | 0 |  | 0 | BLANK |
| 22 A | 145 | 24 | 1 | MARS IV X | 0.1 |  |
| 20 A | 145 | 24 | 1 | MARS IV X | 2 |  |
| 28 A | 145 | 24 | 0 | MARS IV X | 2 | DEEP YELLOW |
| 29 A | 212 | 24 | 0 | MARS IV X | 2 | AMBER |
| 24 A | 145 | 24 | 1 | MARS IV X-2 | 2 |  |
| 25 A | 145 | 24 | 0 | MARS IV X-2 | 2 | DEEP YELLOW |
| 31 A | 212 | 24 | 0 | MARS IV X-2 | 2 | AMBER |
| 31 B | 212 | 24 | 0 | MARS III-B | 2 | AMBER |
| 32 A | 192 | 24 | 1 |  | 0 | CLEAR |
| 32 B | 212 | 24 | 0 |  | 0 | PALE YELLOW |
| 36 A | 205 | 24 | 1 | MARS IV X-2 | 2 | STRAW |
| 37 A | 201 | 24 | 1 | MARS IV X | 2 | AMBER |
| 38 A | 201 | 24 | 1 | MARS III-B | 2 | DARK AMBER |
| 50 A | 201 | 24 | 1 | MARS IV X-2 | 2 | AMBER, —$H_2O$ |

MARS IV X = 4321730P TRILOBE III COMPOSITE FROM RETAIN SAMPLES E326-101
MARS IV X-2 = 4321789FL ZONE 3 COMPOSITE FROM RETAIN SAMPLES E326-106
MARS III-B = 4658831X NPT REACTOR 3 COMPOSITE FROM PLANT E307-119

TABLE I-continued

DBP SOLVENT DECOMPOSITION STUDIES PROTOCOL

| H$_2$O | CATALYST | | TEMPERATURE |
|---|---|---|---|
| 0.0% | III | 0.1 OR 2.0% | 100 |
| 1.0% | IVX | 0.1 OR 2.0% | 145 |
| | IVX2 | 0.1 OR 2.0% | 212 |

TABLE II

COMPOSITION OF DBP SOLVENT AFTER THE TEST

| SAMPLE NUMBER | MAN WT % | PHAN WT % | DBM WT % | DBP WT % | MACD WT % | PACD WT % | FAC WT % | MBP | NET | TOTAL |
|---|---|---|---|---|---|---|---|---|---|---|
| 24 B | 0.01 | 0.01 | 0.01 | 99.94 | 0.01 | 0.01 | 0.01 | 0.01 | <0.01 | 100 |
| 20 B | 0.01 | 0.16 | 0.01 | 99.58 | 0.01 | 0.04 | 0.01 | 0.14 | 0.16 | 100.1 |
| 22 A | 0.01 | 0.17 | 0.01 | 99.6 | 0.01 | 0.01 | 0.01 | 0.13 | <0.01 | 99.95 |
| 20 A | 0.01 | 0.61 | 0.01 | 98.22 | 0.01 | 0.19 | 0.01 | 0.87 | <0.01 | 99.93 |
| 28 A | 0.01 | 0.62 | 0.01 | 98.27 | 0.01 | 0.03 | 0.01 | 0.81 | 0.127 | 99.9 |
| 24 A | 0.01 | 0.58 | 0.01 | 97.87 | 0.01 | 0.25 | 0.01 | 1.21 | 0.05 | 100 |
| 25 A | 0.01 | 0.65 | 0.01 | 98.28 | 0.01 | 0.02 | 0.01 | 0.83 | 0.015 | 99.84 |
| 32 A | 0.01 | 0.1 | 0.01 | 99.51 | 0.01 | 0.13 | 0.01 | 0.09 | N.A. | 99.87 |
| 32 B | 0.01 | 0.58 | 0.01 | 98.17 | 0.01 | 0.64 | 0.01 | 0.17 | N.A. | 99.6 |
| 31 B | 0.01 | 1.14 | 0.59 | 96.84 | 0.01 | 0.41 | 0.01 | 0.69 | 0.54 | 100.2 |
| 29 A | 0.01 | 4.35 | 0.07 | 88.95 | 0.01 | 0.43 | 0.01 | 5.8 | 0.043 | 99.67 |
| 31 A | 0.01 | 5.86 | 0.07 | 85.65 | 0.01 | 0.7 | 0.01 | 7.35 | 0.133 | 99.79 |
| 38 A | 0.01 | 1.54 | 0.01 | 94.13 | 0.01 | 0.41 | 0.01 | 3.65 | 0.4 | 100.2 |
| 37 A | 0.01 | 2.06 | 0.01 | 93.06 | 0.01 | 0.13 | 0.01 | 4.45 | 0.36 | 100.1 |
| 36 A | 0.01 | 4.33 | 0.01 | 85.06 | 0.01 | 0.81 | 0.01 | 9.56 | 0.02 | 99.82 |
| 50 A | 0.01 | 2.13 | 0.03 | 94.92 | 0.01 | 0.31 | 0.01 | 2.24 | 0.17 | 99.83 |

MAN = maleic anhydride
PHAN = phthalic anhydride
DBM = dibutyl maleate
DPB dibutyl phthalate
MACD = maleic acid
PACD = phthalic acid
PAC = fumaric acid
MBP = monobutyl phthalate

TABLE III

COMPOSITION CHANGE BY COMPARISON TO 4658824 B

| SAMPLE NUMBER | COMMENT | PHAN WT % | DBP WT % | PACD WT % | MBP WT % | NET WT % |
|---|---|---|---|---|---|---|
| 24 B | BLANK | 0 | 0 | 0 | 0 | 0 |
| 20 B | BLANK, 145C | 0.15 | −0.36 | 0.03 | 0.13 | 0.16 |
| 22 A | LO IV-X, 145C, H$_2$O | 0.16 | −0.34 | 0 | 0.12 | 0 |
| 20 A | IV-X, 145C, H$_2$O | 0.6 | −1.72 | 0.18 | 0.86 | 0 |
| 28 A | IV-X, 145C | 0.61 | −1.67 | 0.02 | 0.8 | 0.127 |
| 24 A | IV-X2, 145C, H$_2$O | 0.57 | −2.07 | 0.24 | 1.2 | 0.05 |
| 25 A | IV-X, 145C | 0.64 | −1.66 | 0.01 | 0.82 | 0.015 |
| 32 A | BLANK, 192C, H$_2$O | 0.09 | −0.43 | 0.12 | 0.08 | 0 |
| 32 B | BLANK, 212C | 0.57 | −1.77 | 0.63 | 0.16 | 0 |
| 31 B | III-B, 212C | 1.13 | −3.1 | 0.4 | 0.68 | 0.54 |
| 29 A | IV-X, 212C | 4.34 | −11 | 0.42 | 5.79 | 0.043 |
| 31 A | IV-X2, 212C | 5.85 | −14.3 | 0.69 | 7.34 | 0.133 |
| 38 A | III-B, 201C, H$_2$O | 1.53 | −5.81 | 0.4 | 3.64 | 0.4 |
| 37 A | IV-X, 201C, H$_2$O | 2.05 | −6.88 | 0.12 | 4.44 | 0.36 |
| 36 A | IV-X2, 205C, H$_2$O | 4.32 | −14.9 | 0.8 | 9.55 | 0.02 |
| 50 A | IV-X2, 201C, THEN —H$_2$O | 2.12 | −5.02 | 0.3 | 2.23 | 0.17 |

From this data it is was determined that, for a given set of conditions, the presence of water causes more dibutyl phthalate to decompose with an increase in phthalic acid and monobutyl phthalate than where water is absent. Heating dibutyl phthalate by itself to 145° C. for 24 hours causes about as much decomposition as heating with 1% water and 0.1% MARS IV X catalyst. The combination of MARS IV X2 and water gave the highest decomposition of dibutyl phthalate. The effect over 24 hours was relatively slight at 145° C., but more pronounced at 201°–205° C. The effect of temperature at 212° C. gave about as much decomposition in 24 hours as the combination of 145° C. and 1% water.

Although the relative quantitative effects observed in a 24 hour test showed that factors other than the presence of catalyst fines can cause decomposition of dibutyl phthalate, it was concluded that steps should be taken to remove excess catalyst dust from the reaction chamber after charging of catalyst to a reactor, and to prevent formation of fines during operation of the reactor.

EXAMPLE 2

The tubes of several vertical shell and tube reactors were charged with a VPO catalyst made in accordance with U.S. Pat. No. 5,641,722 and sold by Huntsman Corporation under the trade designation MARS V. This catalyst is in the form of trilobes having a principal dimension of about 0.25 inches. The lower heads of the reactors were connected to a source of feed gas comprising n-butane and air, and the upper heads of the reactors were connected to an absorber for recovery of maleic anhydride from the reaction gases by absorption in dibutyl phthalate. In previous operations, it had been observed that gas hour space velocities moderately in excess of normal operating conditions could cause the tops of the columns of catalyst in at least some of the reactor tubes to fluidize or expand the bed volume.

In order to prevent fluidization or expansion of the fixed catalyst bed during further operation of the reactors, and in particular to prevent the catalyst bodies in the fixed catalyst beds from abrading against one another or against the tube walls, a restraining bed comprising discrete bodies of a material substantially denser than the catalyst was placed on the top of the column of catalyst in each tube of the reactors. The restraining bed was 6" in depth and comprised discrete bodies of dense material sold under the trade designation Norton Denstone. The Norton Denstone bodies were in the form of spheres with a principal dimension of 0.25 inches, and had a density of 90 lbs/ft$^3$ (1.44 g/cc). By comparison the bulk density of the VPO catalyst was about 40 lb/ft$^3$ (0.65 g/cc).

To eliminate fines that may have been present in the catalyst as delivered to the reactor site and/or formed by attrition in loading catalyst into the reactor tubes, any fines were substantially removed in the manner illustrated in FIG. 3. Compressed air was blown through the tubes of each reactor to remove dust and fines from the catalyst pack, and the dust laden air stream exiting the top of the reactor was directed to a cartridge filter mounted on a filter truck. Prior to introduction of compressed air into the bottoms of the reactor tubes, the catalyst contained in the tubes was heated to a temperature of about 160° C. by passing hot startup air through the shell of the shell and tube reactor. The de-dusting air flow was introduced into the tubes in successive hour long increments of about at a mass flow rate of about 1.1 (kg/hr) /cm$^2$, equivalent to a linear velocity of about 2.9 m/sec. In each such increment, the air was introduced at an initial mass flow rate of about 0.5 (kg/hr) /cm$^2$, equivalent to an average linear velocity of about 1.4 m/sec., and ramped up to a velocity of 1.1 (kg/hr) /cm$^2$ over a period of about 15 minutes. At the end of each de-dusting air flow increment, the air flow was terminated for 3–5 minutes, then ramped back up to the aforesaid rate. A total of 6–8 air flow increments were used in the de-dusting operation.

De-dusting air exiting the catalyst bed was directed through a process gas cooler where the catalyst dust-laden air was cooled to a temperature of about 90° C., and thence to a bank of cartridge filters mounted on a truck. Upon completion of the operation, the compressed air flow was terminated, and a blower mounted on the truck was used to clear connecting lines of residual catalyst dust. Accumulated catalyst dust was then collected from the cartridge filters by back-pulsing with air using a blower mounted on the truck, and the dust thus recovered conveyed by an auger to a drum used as a receiver therefor. The process gas cooler was washed with deionized water to remove any dust not removed in the line clearing operation.

Thereafter, a nitrogen purge was passed through the catalyst bed while the bed was heated to startup temperature passing first heated air, then high pressure steam, then salt bath through the cooler shell. A reactor feed mixture comprising air and n-butane was then introduced to commence production of maleic anhydride.

During subsequent operations, it was determined that no substantial formation of catalyst fines was caused by abrasion of catalyst resulting from fluidization or expansion of the fixed catalyst beds or any portion thereof. Tar production in the dibutyl phthalate solvent remained low and solvent quality remained good throughout the startup period. The solvent circuit was operated during startup without distillation of solvent or extraction of tars therefrom. After operation for a period of five weeks, the tar content of the solvent was essentially the same as its initial value. By comparison, after the same reactors had been twice previously repacked with catalyst, decomposition of solvent and tar formation had necessitated shutdown of the reactor to prevent further tar production; and it had been necessary to eliminate tars by distillation of the solvent inventory.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A method for preparing a catalytic reactor for use in the production of maleic anhydride by oxidation of a hydrocarbon having at least four carbon atoms in a straight chain, the reactor comprising a reaction chamber containing a fixed catalyst bed having active sites comprising a phosphorus vanadium oxide catalyst, the method comprising:

passing a purging gas through the reaction chamber for removal from said reaction chamber of phosphorus vanadium oxide catalyst fines contained therein while not removing said fixed bed of catalyst bodies from said chamber; and separating said fines from the purging gas exiting said reaction chamber to substantially prevent emission of phosphorus vanadium oxide catalyst fines into the atmosphere.

2. A method as set forth in claim 1 wherein said purging gas comprises air, and said catalyst bed is heated to a temperature of at least 120° C. prior to passing said purging gas through said reaction chamber so as to prevent absorption of moisture from the purging air into said catalyst bed.

3. A method as set forth in claim 2 wherein said purging gas comprises compressed air.

4. A method as set forth in claim 1 wherein said purging gas has a dew point not greater than about 10° C.

5. A method as set forth in claim 1 wherein said purging gas is passed through said catalyst bed at a linear flow velocity sufficient to fluidize said catalyst fines but not sufficient to fluidize the catalyst bodies of said fixed catalyst bed.

6. A method as set forth in claim 5 wherein said velocity is sufficient to fluidize fines having a particle size of less than 100$\mu$ but insufficient to fluidize a bed constituted of catalyst bodies having an average body volume of greater than 0.02 cc.

7. A method as set forth in claim 1 wherein said purging gas is passed through said catalyst bed at a linear flow velocity of at least 0.5 times the normal velocity of reaction gases during operation of said reactor for the production of maleic anhydride.

8. A method as set forth in claim 1 wherein said purging gas is passed through said catalyst bed at a linear superficial flow velocity of at least 1.4 m/sec.

9. A method as set forth in claim 8 wherein said purging gas is passed through said catalyst bed in intermittent increments.

10. A method as set forth in claim 9 wherein each increment comprises passing purging gas through said catalyst bed for a period of between about 0.2 hr and about 2 hr.

11. A method as set forth in claim 10 wherein said purging gas is passed through said catalyst bed in at least two discrete increments.

12. A method as set forth in claim 6 wherein the direction of flow of purging gas through said catalyst bed is periodically reversed.

13. A method as set forth in claim 1 wherein said reaction chamber comprises a plurality of tubes in a shell and tube heat exchanger.

14. A method as set forth in claim 13 wherein catalyst fines are removed from said reaction chamber after filling of the tubes with catalyst but before the catalyst has been used in the oxidation of hydrocarbon to produce maleic anhydride.

15. A method as set forth in claim 1 wherein said filter comprises a filter medium having a pore size of no greater than about $50\mu$.

16. A method as set forth in claim 1 wherein said filter comprises a portable filter temporarily connected to a port of said reaction chamber on the opposite side of said bed from another port of said reaction chamber into which the purging gas flows, said filter being disconnected from said reactor after removal of fines from said reaction chamber.

17. A method as set forth in claim 16 wherein said filter is mounted on a vehicle.

18. A method as set forth in claim 16 wherein said filter is skid mounted.

19. Apparatus for removal of catalyst fines from a fixed catalyst bed comprising discrete bodies of phosphorus vanadium oxide catalyst, the apparatus comprising:

a reaction chamber containing said fixed bed, said reaction chamber comprising a gas inlet and a gas outlet;

a source of purging gas in fluid flow communication with an inlet of said reaction chamber, said source being capable of supplying said purging gas at a velocity effective to entrain catalyst fines having a particle size less than about $100\mu$ and remove said fines from said catalyst bed; and a filter in fluid flow communication with an outlet of said reaction chamber, said filter comprising a porous filter medium the pore size of which is effective to substantially remove entrained catalyst fines from said purging gas.

20. An apparatus as set forth in claim 19 further comprising means for heating and maintaining said fixed bed at a temperature of at least about 150° C. during passage of purging gas therethrough.

21. An apparatus as set forth in claim 19 wherein said filter is effective to substantially remove at least about 99% by weight of fines entrained in said purging gas.

22. An apparatus as set forth in claim 21 wherein said filter is effective to remove fines having a particle size greater than about $20\mu$.

23. An apparatus as set forth in claim 19 further comprising a gas cooling heat exchanger in fluid communication with said reaction chamber and said filter, and positioned therebetween and in series therewith with respect to flow of catalyst fine-laden purging gas exiting said reaction chamber, and means for delivering a cooling medium to said gas cooling heat exchanger, said gas cooling heat exchanger having cooling capacity sufficient to cool said catalyst fine-laden purging gas to a temperature not greater than about 110° C.

24. An apparatus as set forth in claim 19 wherein said source of purging gas is capable of supplying said purging gas at a velocity effective to entrain catalyst fines having a particle size less than about $1000\mu$.

\* \* \* \* \*